(12) United States Patent
Licato et al.

(10) Patent No.: US 7,606,614 B2
(45) Date of Patent: Oct. 20, 2009

(54) PREDICTION METHODS AND APPARATUS

(75) Inventors: Paul Edgar Licato, Wauwatosa, WI (US); Marcela Alejandra Gonzalez, Waukesha, WI (US); Mukta Chandrashekhar Joshi, Belmont, MA (US); Mark Vincent Profio, Elm Grove, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/512,539

(22) Filed: Aug. 30, 2006

(65) Prior Publication Data

US 2008/0097196 A1    Apr. 24, 2008

(51) Int. Cl.
*A61B 6/00* (2006.01)
(52) U.S. Cl. ............... 600/431; 600/420; 600/425; 600/458; 378/66
(58) Field of Classification Search ............... 600/431, 600/458, 420, 419, 425; 328/66
See application file for complete search history.

(56) References Cited

U.S. PATENT DOCUMENTS

| | | | | |
|---|---|---|---|---|
| 5,262,946 A | * | 11/1993 | Heuscher | 378/15 |
| 5,301,672 A | * | 4/1994 | Kalender | 600/428 |
| 5,459,769 A | * | 10/1995 | Brown | 378/4 |
| 6,061,590 A | | 5/2000 | Krivitski | 600/431 |
| 6,167,293 A | * | 12/2000 | Chenevert et al. | 600/420 |
| 6,337,992 B1 | * | 1/2002 | Gelman | 600/425 |
| 6,597,936 B1 | * | 7/2003 | Liu et al. | 600/420 |
| 7,001,359 B2 | | 2/2006 | Rogers | 604/118 |

* cited by examiner

*Primary Examiner*—Eric F Winakur
(74) *Attorney, Agent, or Firm*—ZPS Group, SC (57) ABSTRACT

A method includes predicting a contrast bolus arrival time, and performing at least one of the following: a) automatically switching from a monitor phase to a scan phase at the predicted arrival time; and b) prompting a user to began a scan at the predicted arrival time.

12 Claims, 8 Drawing Sheets

Figure 5. Example of the derivative function for a given Time Intensity Curve.

PREDICTION METHODS AND APPARATUS

BACKGROUND OF THE INVENTION

This invention relates generally to diagnostic imaging methods and apparatus, and more particularly, to methods and apparatus that provide for the prediction of a bolus's arrival in a region of interest.

Contrast Enhanced Angiography studies are an important clinical tool that provide a way to monitor the arrival of contrast agents for CT Angiographic (CTA) applications. When the mean signal intensity over a user defined region of interest (ROI) reaches a pre-defined threshold, the operator can initiate the CT scan to capture arterial phase images. It is desirable to image the vasculature of interest while the contrast bolus resides in the arterial system, prior to parenchymal and venous enhancement (so-called "venous contamination"). Therefore, the primary challenge in CTA imaging is to time the CT (Computed Tomography) scan to coincide with the peak contrast bolus in the arterial system.

This tool is available today in the General Electric Company's CT scanner and it is called SmartPrep. Since its introduction well over a decade ago, SmartPrep has become an indispensable tool to customers, and is used many times daily at sites throughout the world. A SmartPrep protocol consist of two scan phases; one called "Monitor phase", where the user observes the progress of the contrast in the ROI and "Scan phase" when the actual scan of the ROI occurs according to protocol selected.

The current SmartPrep feature does a good job of monitoring the contrast dynamics over a small ROI in some applications, but the time to transition from the monitor mode to the scan mode may be too long and variable for some clinical situations. Therefore, it would be desirable to shorten the transition time from the monitor mode or phase to the scan mode or phase. Imaging the carotid arteries, for example, requires a very short monitor-to-scan delay, on the order of a second or two, to minimize venous contamination. Furthermore, increases in scanner performance in terms of slice coverage and rotation speed demand shorter latencies and more precise timing control. This is particularly true in the case of the LightSpeed 64 and 32 Scanners commercially available from the General Electric Healthcare business of The General Electric Company. In addition, the time to move the table from the monitor location to the beginning of the scan location adds to the overall latency.

BRIEF DESCRIPTION OF THE INVENTION

In one aspect a method includes predicting a contrast bolus arrival time, and performing at least one of the following: a) automatically switching from a monitor phase to a scan phase at the predicted arrival time; and b) prompting a user to began a scan at the predicted arrival time.

In another aspect, a computer readable medium is embedded with a program. The program is configured to instruct a computer to receive patient data, and predict a bolus transit time based on the received data.

In yet another aspect, a system includes an x-ray source, an x-ray detector positioned to receive x-rays emitted from the source, and a computer operationally coupled to the source and the detector. The computer is configured to predict a contrast bolus arrival time, and perform at least one of the following: a) automatically switch from a monitor phase to a scan phase at the predicted arrival time; and b) prompt a user to began a scan at the predicted arrival time.

In still another aspect, a method is provided for reducing a delay in a contrast study wherein an imaging system includes a plurality of rows in a detector, and wherein a starting slice location for a scan phase is in a different plane than a monitor plane. The method includes acquiring a monitor scan with rows closest to the start of the scan phase.

In yet still another aspect, a method includes alerting a patient prior to a predicted bolus peak.

DETAILED DESCRIPTION OF THE INVENTION

There are herein described methods and apparatus useful for imaging systems such as, for example, but not limited to an x-ray system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention. Although, described in the setting of an x-ray system, it is contemplated that the benefits of the invention accrue to all diagnostic imaging systems and modalities such as PET, MRI, SPECT, Ultrasound, fused systems such as a CT/PET system, and/or any modality yet to be developed in which boluses are used.

Figure 1:
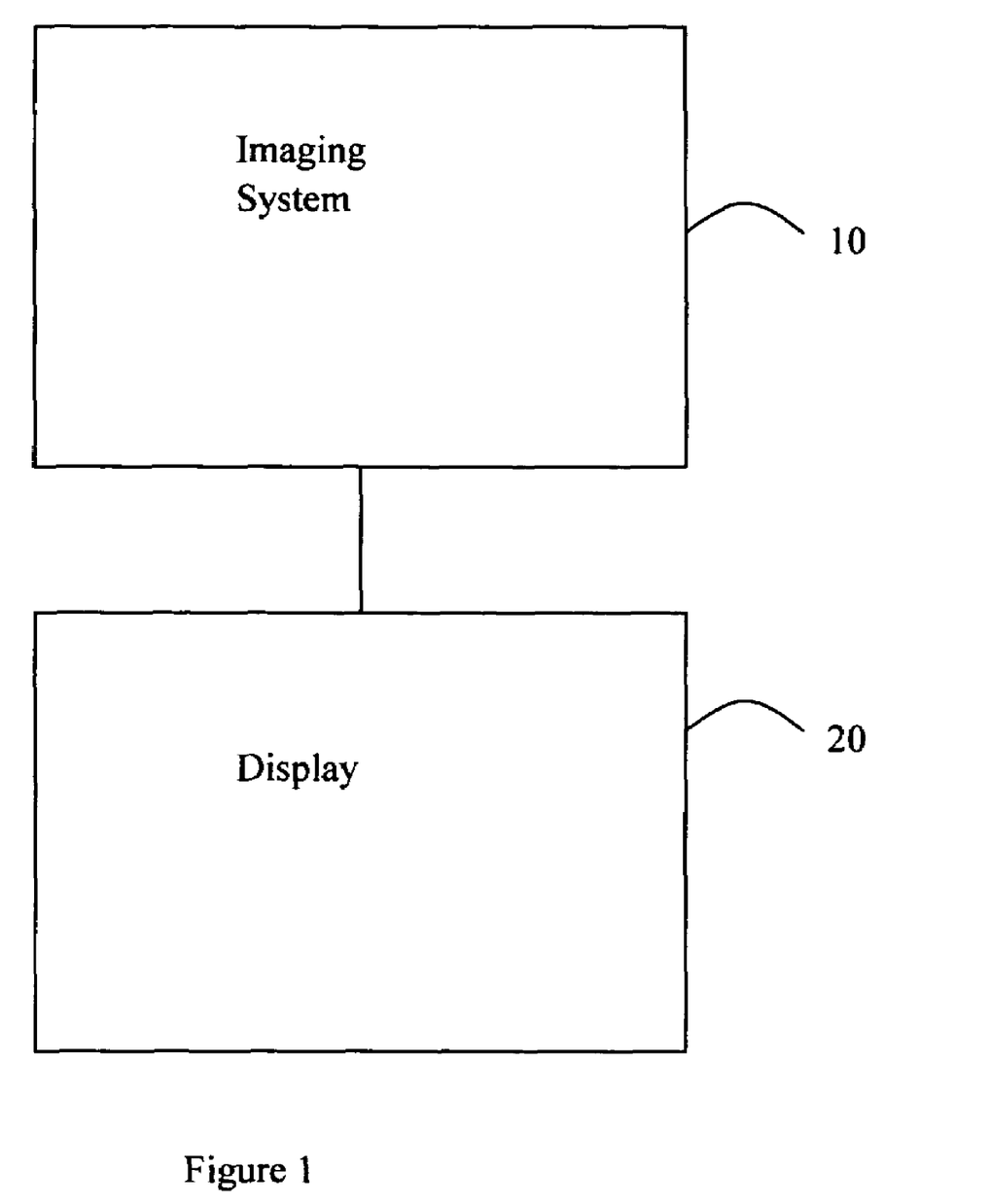
FIG. 1 illustrates an exemplary diagnostic imaging system.

FIG. 1 illustrates an imaging system 10 with an associated display 20. Imaging system 10 can be of any modality, but in one embodiment, system 10 is a CT system. In another embodiment, system 10 is a dual modality imaging system such as a combined CT/PET system and the below described prediction of a bolus's arrival in a ROI can be done in one modality (e.g., CT) and the processed data can be transferred to the other modality (e.g., PET). Display 20 can be separate from system 10 or integrated with system 10. System 10 includes an acquisition device such as an x-ray radiation detector, a Gamma Camera, an ultrasound probe and/or an MRI coil.

The x-ray imaging system includes a processing circuit. The processing circuit (e.g., a microcontroller, microprocessor, custom ASIC, or the like) is coupled to a memory and a display device. The memory (e.g., including one or more of a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, or an other digital source such as a network or the Internet, as well as yet to be developed digital means, and the like) stores imaging data.

The memory may also store a computer program including instructions executed by the processing circuit to implement the functions described herein. The processing circuit provides an image for display on a device. The detector may be a flat panel solid state image detector, for example, although conventional film images stored in digital form in the memory may also be processed. In one embodiment, the processing circuit executes instructions stored in firmware (not shown).

Of course, the methods described herein are not limited to practice in system 10 and can be utilized in connection with many other types and variations of imaging systems. In one embodiment, the processing circuit is a computer that is programmed to perform functions described herein, and, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a human patient setting, it is contemplated that the benefits of the invention accrue to non-human imaging systems such as those systems typically employed in small animal research.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

The herein described methods and apparatus provide for an automated detection of a bolus's arrival at a region of interest (ROI).

The prediction of peak bolus signal may be based on contrast measurements, may be based on a slope change in a time intensity (HU (Hounsfield Units)) curve and/or may be based on exceeding a pre-defined HU threshold.

Figure 2:
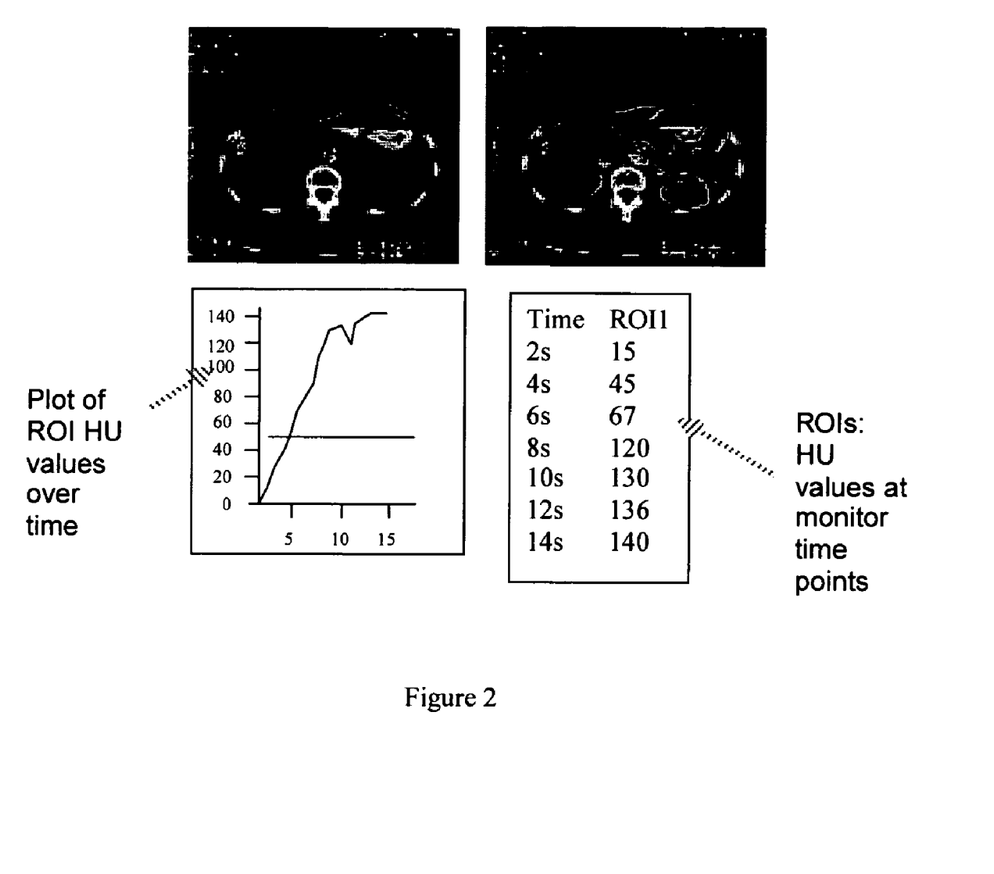
FIG. 2 illustrates a graph that is presented plotting HU values versus time, with a horizontal line at the desired HU value level.

One known system allows the user to enter a threshold enhancement value, that is the difference between the baseline value and the desired enhancement value. FIG. 2 illustrates a graph that is presented plotting HU value versus time, with a horizontal line at the desired HU value level. When the HU value reaches the HU threshold line, the user then selects Scan phase to start the scan. Automated detection of bolus arrival or Auto-Scan trigger would anticipate and thus improve/reduce system turn-around time from the monitor mode to the scan mode, therefore, significantly improving the accuracy of the scan phase transition. This function is referred to as Auto-trigger.

Auto-trigger, as well as anticipation of threshold value, are desirable for Enhanced SmartPrep and Real-Time Smartprep.

The operator also has the option to trigger the Scan phase at any time, even prior to the automated peak detection. Similarly, the operator can choose to suspend the automatic triggering, delaying the start of the Scan phase for as long as desired.

During an Auto-trigger defined protocol, the user may still enter a desired value for the enhancement threshold, expressed either as HU value or a percent increase from baseline, and manually start the scan, just as in the current Smartprep. Once the enhancement level for the monitor ROI (s) reaches the user entry (HU value or the % increase translated to HU from the baseline value), the scan acquisition will switch from the monitor phase to the scan phase automatically.

Anticipated auto-trigger may provide the function of predicting either the time to reach the desired enhancement threshold, or the approach to the peak of the enhancement curve.

There are Three Approaches Presented Here.

Figure 3:
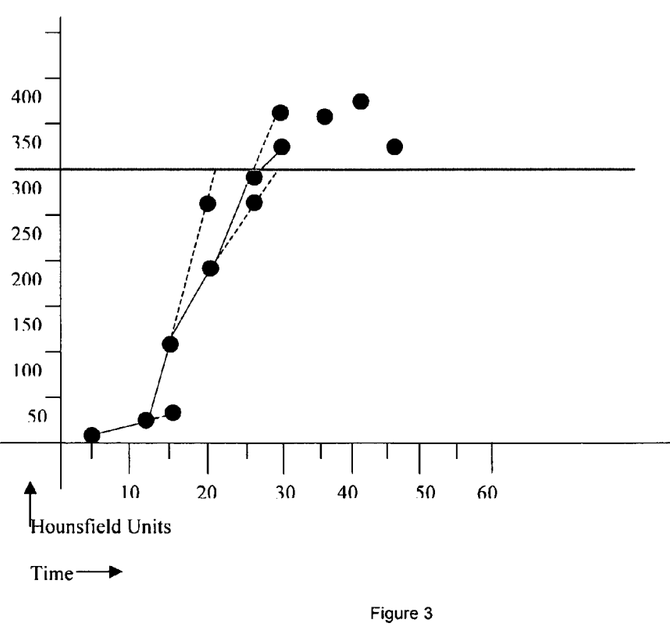
FIG. 3 illustrates that this slope can be used to predict the amount of time it will take to reach the user entered threshold target.

Approach 1. Based on slope change in time intensity (HU) curve: The slope of HU value enhancement over time may be calculated from the two most recently acquired data points. FIG. 3 illustrates that this slope can be used to predict the amount of time it will take to reach the user entered threshold target.

Once the percentage error between the predicted and actual values of enhancement is within 10%, the transition to scan phase will be initiated when the predicted time to reach the threshold equals the diagnostic delay time. As used herein the "diagnostic delay time" is the time between a user pressing the scan button and when the scan data is first acquired. Additionally, in the automated case, the "diagnostic delay time" is the time between the computer or other processing circuit issuing a scan command and when the scan data is first acquired. The diagnostic delay time can be added to the predicted bolus transit time to obtain a scan initiate time.

The time calculation can be a simple conversion of the slope equation, with the slope equating to the change in enhancement divided by the change in time.

$$\text{slope}(t_n) = \frac{\text{value}(t_n) - \text{value}(t_{n-1})}{t_n - t_{n-1}}$$

$$\text{predicted value}(t) = \text{slope} * t + K$$

$$\% \text{ error} = \frac{actualValue(t) - predictedValue(t)}{actualValue(t)} * 100$$

$$predictedTime(t) = \frac{thresholdHU - K}{\text{slope}(t)}$$

Where k is the HU at the start of the scan t=0 (i.e., k is the baseline reference).

Figure 4:
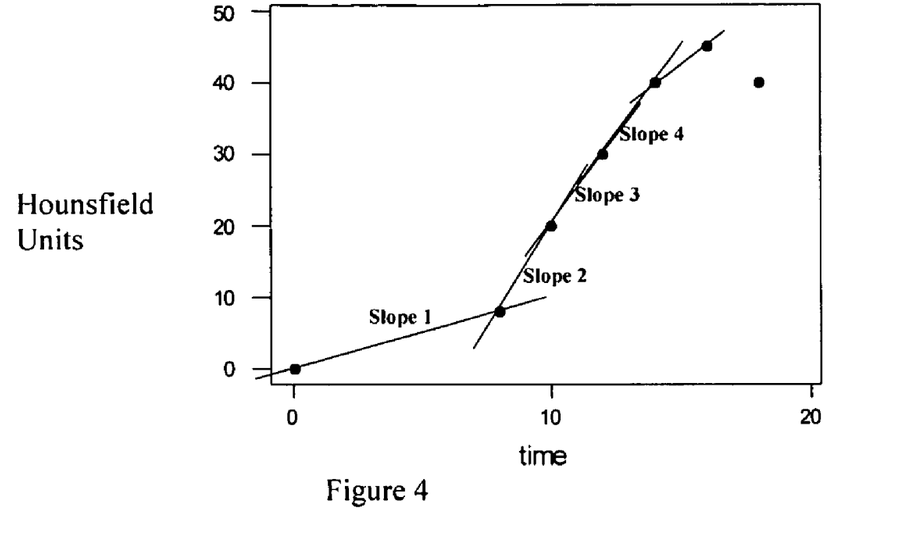
FIG. 4 illustrates that the trigger could be initiated from consecutive declines in the value of the derivative function.
Figure 5:
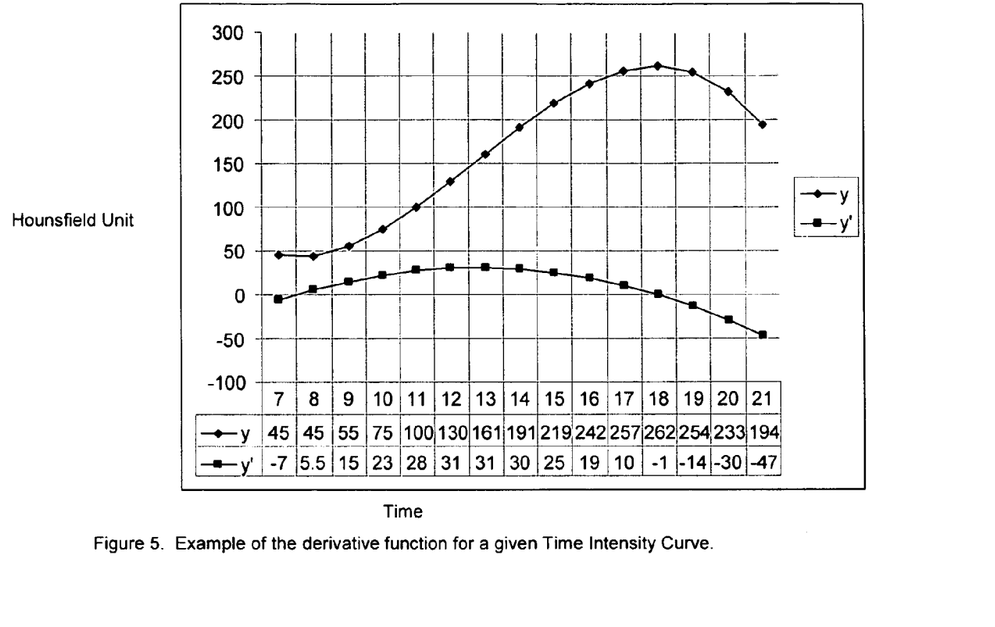
FIG. 5 illustrates an example of the derivative function for a given Time Intensity Curve.

Approach 2. Based on exceeding a pre-defined HU threshold: This additional potential mechanism for auto-triggering requires the creation of a function to fit the data points of HU values acquired during the scan. In most cases, the equation is a cubic function, but it could also be expressed as any polynomial expression. When the enhancement is reaching the peak, the slope of the curve begins to decrease. Thus, the derivative of this enhancement function will generally be increasing for early time points, and then begin to decrease several seconds before the peak is reached (see FIG. 3). FIG. 4 illustrates that the trigger could be initiated from consecutive declines in the value of the derivative function. This analysis could be used in conjunction with the slope measure, as an additional check. In other words, the slope of the derivative should be decreasing as the enhancement approaches peak. FIG. 5 illustrates an example of the derivative function for a given Time Intensity Curve. This analysis also has the potential for predicting the onset of the peak enhancement without requiring a desired threshold user input. Moreover, the desired threshold could be estimated on anatomy to be scanned, protocol prescribed, patient parameters (weight, sex, age, cardiac rate, etc.).

Figure 6:
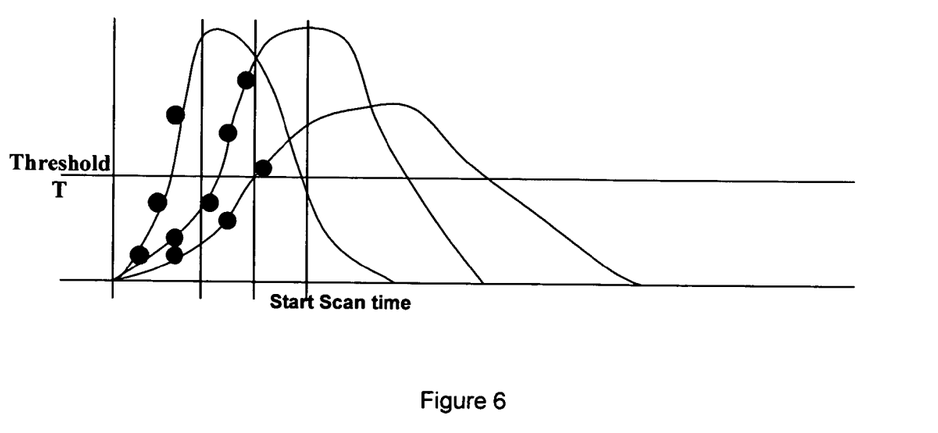
FIG. 6 illustrates that this threshold could be at a user specified value or an empirically defined value as mentioned in method 2 (i.e., approach 2).

Approach 3. Based on the slope at the time a given HU threshold is reached: This alternative method would make the delay to start the scanning phase inversely proportional to the slope at the time a threshold is reached. FIG. 6 illustrates that this threshold could be at a user specified value or an empirically defined value as mentioned in method 2 (i.e., approach 2).

The start scan time (t) is given by the following $$t = \frac{1}{\text{slope}(t_T)} + \text{scanner\_delay}$$

Fast Transition to Angio Scan to Capture Arterial Phase Images

An additional application is imaging of the carotid and circle of willis vasculature in the neck and head regions. In many vascular imaging protocols, it is desirable to acquire during the arterial phase and before the venous phase begins so that the arteries are more clearly visualized. That is, the scan acquisition is completed while the contrast enhancement in the arteries is at a peak, and before any contrast has started to return through the veins. Given the short transit time through the brain, this acquisition needs to be completed in approximately 5 seconds Improved Image Quality (IO) in Region of Interest Optimizing the detection of contrast peak significantly improves the image quality as the volume or region of interest are scanned during the maximum contrast enhancement. This can also lead to reduction in technique factors improving the X-ray dose delivered to the patient.

Being Able to Play Voice Promoting Command to Patient in Advance of Peak Bolus Detection to Further Improve IO and Patient Comfort Being able to alert the patient seconds before the peak detection makes the patient experience more comfortable and limits how long they need to hold their breath. It also reduces the time they need to hold still ensuring less motion during the critical section of the exam process.

Figure 7:
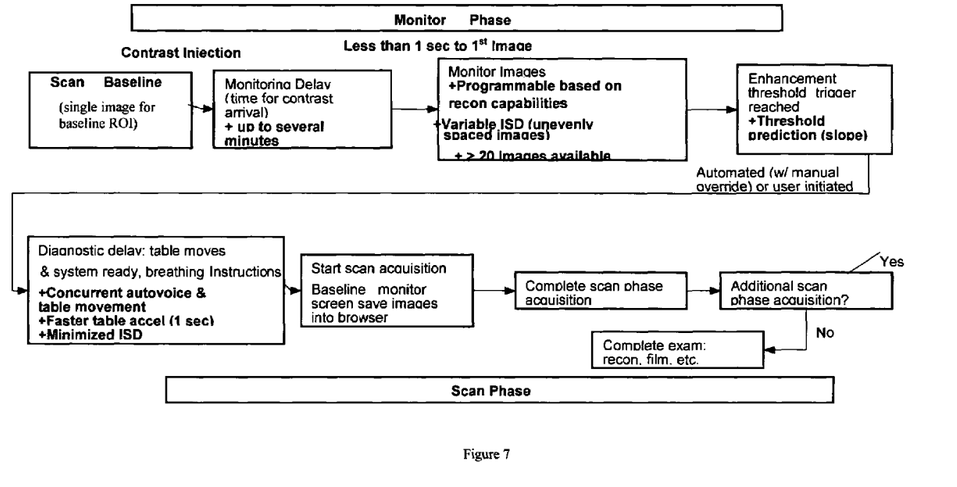
FIG. 7 illustrates a single triggered exam.
Figure 8:
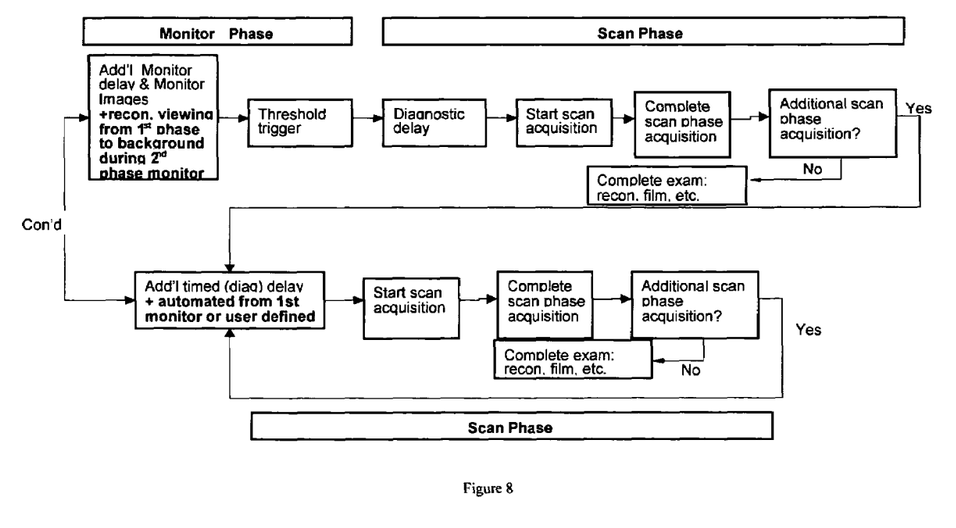
FIG. 8 illustrates a multiple triggered exam.

FIG. 7 illustrates a single triggered exam wherein ISD refers to interscan delay. There is additional need for multiple triggers in a SmartPrep study for particular applications. FIG. 8 illustrates a multiple triggered exam. For example, a dual-phase liver study aims to acquire data during arterial and venous enhancement phases. Thus the capability for Smart-Prep to monitor and trigger acquisition during the first scan group (arterial phase), and then again during the second scan group (venous phase) is desired. The additional trigger may or may not require an additional monitor phase, depending on the study. For the case where no additional monitor is required, the time from start injection or time from start of the first phase would be used to trigger the additional scan phase. There may also be the case of an additional monitor phase at a different location, such as an abdomen/chest acquisition followed by a lower extremity runoff. For those cases, an additional monitor may be required before the extremity acquisition to ensure peak enhancement for that part of the acquisition. See this process described in FIG. 8.

Adaptive Algorithm

Another aspect of the invention is the ability to store Monitor phase data along with patient demographic data (e.g. gender, age, weight, height, etc.). These data are stored in a database and can be statistically analyzed and grouped to predict likely bolus transit times based on the demographic data. The customer can use this "expert system" to make bolus transit predictions based on their patient population.

End Slice Monitoring to Decrease Z-Algorithm

The VCT detector is comprised of 64 0.625 mm rows. Today, the monitor scan is taken from the 16 central rows, resulting in a 10 mm slice thickness. Typically, the monitor plane location is different from the starting slice location of the Scan phase. By acquiring the monitor scan with the 16 rows closest to the start of the Scan phase, then the table travel distance can be reduced by up to 15 mm.

With larger detector arrays, this benefit will increase accordingly. The herein described methods and apparatus automate the monitoring and detection of peak arterial contrast during a CT angiography exam and initiates the acquisition of the arterial phase 3D image. Without this technology, technologists are required to intently focus on the monitor images and quickly determine when the Scan acquisition should be manually started. It is easy to trigger too early or too late using this current method, unless the operator is experienced.

The herein described methods and apparatus introduces different Contrast Predicting Models to estimate the amount of contrast needed for optimal image quality based on predictions and not on a user-defined threshold.

The predicting models are designed on the idea of calculating the specific threshold value automatically based on scan parameters, patient parameters, anatomy to be studied, and/or future estimation of contrast level. By providing a more scientific approach in the calculation of the triggering levels, systematic and reliable results are obtained improving image quality for contrast enhanced studies and decreasing radiation to the patient.

The ability to automatically trigger the scan phase event will provide superior synchronized timing for contrast peak, which will result in enhanced IQ for the given ROI.

Technical effects include that the herein described methods and apparatus will reduce or eliminate operator errors as well provide for more consistent results between exams.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method comprising:
   injecting a subject with a contrast bolus;
   predicting a contrast bolus arrival time at a region of interest, said predicting comprising monitoring a slope change of a time intensity curve and monitoring a derivative of the slope for consecutive declines in value; and
   performing at least one of the following:
   a) automatically switching from a monitor phase to a scan phase at the predicted arrival time; and
   b) prompting the user to begin a scan at the predicted arrival time.

2. A method in accordance with claim 1 wherein the predicted arrival time incorporates a diagnostic delay time.

3. A method in accordance with claim 1 wherein said monitoring comprises comparing a predicted enhancement value to an actual enhancement value.

4. A method in accordance with claim 1 wherein said predicting comprises at least partially basing the prediction on at least one of an anatomy to be scanned, a protocol prescribed, and a patient parameter.

5. A computer readable medium embedded with a program configured to instruct a computer to:
   receive data related to a contrast bolus injected into a patient; and
   predict a bolus transit time to a region of interest based on the received data by monitoring a slope change of a time intensity curve and a derivative of the slope for consecutive declines in value.

6. A medium in accordance with claim 5 wherein said program is further configured to compare the received data with a database comprising demographic data.

7. A medium in accordance with claim 6 wherein said program is further configured to add a diagnostic delay time to the predicted bolus transit time to obtain a scan initiate time.

8. A medium in accordance with claim 7 wherein said program further is configured to instruct the computer to perform at least one of the following:
   a) automatically switch from a monitor phase to a scan phase at the scan initiate time; and
   b) prompt a user to began a scan at the scan initiate time.

9. A medium in accordance with claim 8 wherein said program further is configured to instruct the computer to compare a predicted enhancement value to an actual enhancement value.

10. A medium in accordance with claim 5 wherein said program is further configured to instruct the computer to at least partially base the prediction on at least one of an anatomy to be scanned, and a protocol prescribed.

11. A system comprising:
    an x-ray source;
    an x-ray detector positioned to receive x-rays emitted from said source; and
    a computer operationally coupled to said source and said detector, said computer configured to:
    predict a contrast bolus arrival time at a region of interest by monitoring a slope change of a time intensity curve and a derivative of the slope for consecutive declines in value; and
    perform at least one of the following:
    a) automatically switch from a monitor phase to a scan phase at the predicted arrival time; and
    b) prompt a user to began a scan at the predicted arrival time.

12. A system in accordance with claim 11 wherein said computer is further configured to compare a predicted enhancement value to an actual enhancement value.

* * * * *

UNITED STATES PATENT AND TRADEMARK OFFICE
CERTIFICATE OF CORRECTION

PATENT NO. : 7,606,614 B2
APPLICATION NO. : 11/512539
DATED : October 20, 2009
INVENTOR(S) : Licato et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 10 days.

Signed and Sealed this

Twelfth Day of October, 2010

David J. Kappos
*Director of the United States Patent and Trademark Office*